(12) United States Patent
Han et al.

(10) Patent No.: US 7,129,363 B2
(45) Date of Patent: Oct. 31, 2006

(54) CONDUCTIVE COMPOUND, ELECTRODE AND SENSOR CONTAINING THE SAME, AND TARGET MOLECULE DETECTION METHOD USING THE SENSOR

(75) Inventors: Jung-im Han, Seoul (KR); Jun-hoe Cha, Gyeonggi-do (KR); Geun-bae Lim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 409 days.

(21) Appl. No.: 10/791,524

(22) Filed: Mar. 1, 2004

(65) Prior Publication Data
US 2004/0175747 A1  Sep. 9, 2004

(30) Foreign Application Priority Data
Mar. 7, 2003  (KR) ............ 10-2003-0014482

(51) Int. Cl.
C07D 333/38  (2006.01)
C08F 26/06   (2006.01)
C12M 3/00    (2006.01)
G01N 1/00    (2006.01)

(52) U.S. Cl. ............... 549/71; 526/258; 435/287.9; 204/403.11

(58) Field of Classification Search ............ 549/71; 526/258; 435/287.9; 204/403.11
See application file for complete search history.

(56) References Cited

U.S. PATENT DOCUMENTS

| | | | |
|---|---|---|---|
| 6,201,086 B1 | 3/2001 | Garnier ............ 526/258 |
| 6,825,358 B1* | 11/2004 | Afzali-Ardakani et al. ... 549/59 |
| 6,878,801 B1* | 4/2005 | Fujiki et al. .......... 528/380 |
| 6,890,715 B1* | 5/2005 | Lewis et al. .............. 435/6 |
| 6,913,710 B1* | 7/2005 | Farrand et al. ........ 252/299.61 |
| 6,936,190 B1* | 8/2005 | Yoshida ................ 252/511 |
| 6,984,737 B1* | 1/2006 | Hartmann et al. ........ 549/68 |
| 7,014,796 B1* | 3/2006 | Jen et al. ................ 252/582 |
| 7,015,336 B1* | 3/2006 | Reed et al. ............. 549/59 |
| 7,029,606 B1* | 4/2006 | Dalton et al. .......... 252/582 |
| 7,033,727 B1* | 4/2006 | Kodama .............. 430/270.1 |
| 7,057,054 B1* | 6/2006 | Irie .................... 549/59 |

FOREIGN PATENT DOCUMENTS

EP  1 347 463 A2  9/2003
WO  WO 00/31750  6/2000

OTHER PUBLICATIONS

European Search Report EP 04 00 5433, date of completi n of the search Jun. 3, 2004.
"Specific Recognition of Nucleobase-Functionalized Polythiophenes"; Authors: Peter Bauerle and Andreas Emge; WILEY-VCH Verlag GmbH, D-69469 Weinheim; Advanced Materials, vol. 3, No. 4; 1998; pp. 324-330.

* cited by examiner

Primary Examiner—Deborah C. Lambkin
(74) Attorney, Agent, or Firm—Cantor Colburn LLP

(57) ABSTRACT

A conductive compound of formula (I) below, an electrode coated with the conductive compound, a sensor including the electrode, and a target molecule detection method using the sensor are provided:

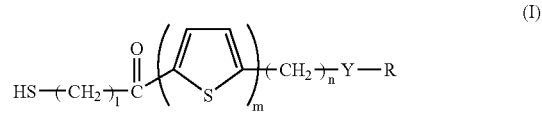

(I)

wherein Y is a carbonyl or —NH—; R is one of H, OH, a leaving group, and a probe group; l is an integer from 3 to 6; m is an integer from 1 to 4; and n is an integer from 0 to 3.

15 Claims, 4 Drawing Sheets

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:

<223> OTHER INFORMATION: ssDNA probe having amino group at its 5' terminus.

<400> SEQUENCE: 1
gttcttctca tcatc                                                    15

CONDUCTIVE COMPOUND, ELECTRODE AND SENSOR CONTAINING THE SAME, AND TARGET MOLECULE DETECTION METHOD USING THE SENSOR

BACKGROUND OF THE INVENTION

This application claims the priority of Korean Patent Application No. 2003-14482, filed on Mar. 7, 2003, in the Korean Intellectual Property Office, the disclosure of which is incorporated herein in its entirety by reference.

1. Field of the Invention

The present invention relates to a novel conductive compound, an electrode coated with the compound, a sensor including the electrode, and a target molecule detection method using the sensor.

2. Description of the Related Art

There have been many studies on the development of biomolecule detecting sensors based on the electrochemical principles. One advantage of using the electrochemical principles lies in that sensors can be miniaturized. Accordingly, there have been great advances in research into electrochemical sensors, such as ionic sensors, gas sensors, biosensors, etc. In the fields of genomics and proteomics, it is very important to monitor information on the hybridization of DNA, among other biological molecules, and to monitor conformational changes of proteins. To this end, there have been developed sensors using electrochemically active organic substance and sensors using conductive polymers. In particular, intercalator-based sensors are ready to be released on the market as a result of extensive research thereon.

In conductive polymer sensors, only a few representative monomers capable of being polymerized on electrodes are available, and it is difficult to control the physical properties of polymers. As a result, research into the conductive polymer sensor has been relatively slow. Representative conductive polymer sensor materials include pyrroles, thiophenes, anilines, and the like. However, because anilines can only be used in acidic conditions, pyrroles and thiophenes have been the main focus of research.

However, pyrroles cannot be used for a long duration due to low redox potential (U.S. Pat. No. 6,201,086). Thiophenes have a higher redox potential but are more hydrophobic than pyrroles, so they are unsuitable for water-based biomolecule systems (Bauerle P. and Emge A., Adv. Materi., 3:324 (1998)).

Another problem arising with conductive polymer sensors lies in that the chain length of polypyrroles or polythiophenes cannot be controlled, disabling formation of an even, thin polymer layer. Therefore, such conductive polymer sensors are unsuitable for detecting trace of a target molecule, such as DNA, which is essentially dispersed. Moreover, due to the difficulty in controlling the chain length of the conductive polymers, signals generated as a result of a reaction between the target molecule and the conductive polymer layer are not reproducible.

SUMMARY OF THE INVENTION

The present invention provides a novel conductive compound capable of forming a self-assembled monolayer having a uniform thickness.

The present invention also provides an electrode coated with the conductive compound and a sensor including the electrode.

The present invention also provides a target molecule detection method using the sensor.

According to an aspect of the present invention, a conductive compound of formula (1) below is provided:

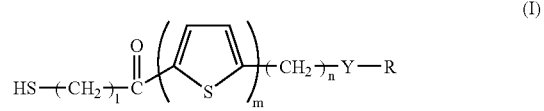

(I)

wherein Y is a carbonyl or —NH—; R is one of H, OH, a leaving group, and a probe group; l is an integer from 3 to 6; m is an integer from 1 to 4; and n is an integer from 0 to 3.

According to one aspect of the present invention, a method of synthesizing the conductive compound of said formula (I) by reacting a compound of formula (IV) below with thiourea is provided:

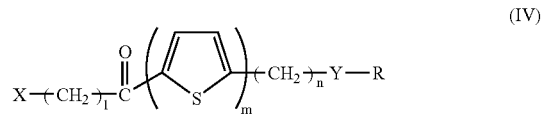

(IV)

wherein Y is carbonyl or —NH—, R is one of H, OH, a leaving group, and a probe group, X is halogen atom, l is an integer from 3 to 6, m is an integer from 1 to 4, and n is an integer from 0 to 3.

According to another aspect of the present invention, a method of synthesizing the conductive compound of formula (I), comprising reacting a compound of formula (V) below with a compound of formula (VI) below is provided:

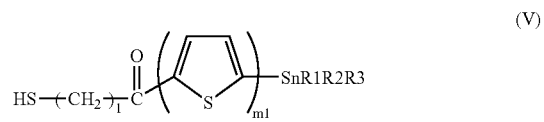

(V)

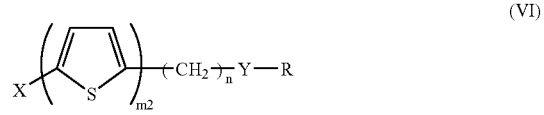

(VI)

wherein R1, R2, and R3 are independently $C_1$–$C_8$ alkyl groups; Y is carbonyl or —NH— group; R is one of H, OH, a leaving group, and a probe group; X is a halogen atom; l is an integer from 3 to 6; m1 and m2 are integers from 1 to 4 and $2 \leq m1+m2 \leq 4$; and n is an integer from 0 to 3.

According to still another aspect of the present invention, an electrode coated with the conductive compound of said formula (I), wherein the electrode being made of gold is provided.

According to still another aspect of the present invention, a sensor including an electrode coated with the conductive compound of said formula (I), wherein the electrode being made of gold is provided.

According to still another aspect of the present invention, a target molecule detection method comprising the following steps is provided:

(a) immobilizing a compound of formula (I) below on a gold substrate to form a self-assembled monolayer;

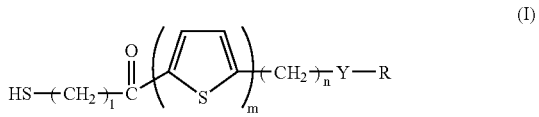

wherein Y is a carbonyl or —NH—; R is one of H, OH, a leaving group, and a probe group; l is an integer from 3 to 6; m is an integer from 1 to 4; and n is an integer from 0 to 3;

(b) reacting a surface of the self-assembled monolayer with probes;

(c) contacting a target molecule capable of specifically binding to the probes with the probes in the self-assembled monolayer; and (d) measuring an electrical signal from the target molecule-probe complex.

According to still another aspect of the present invention, a target molecule detection method comprising the following steps is provided:

(a) immobilizing a compound of formula (I) below on a gold substrate to form a self-assembled monolayer;

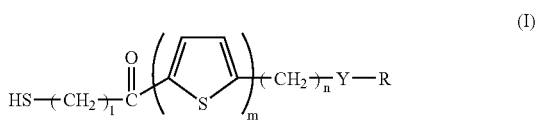

wherein Y is a carbonyl or —NH—; R is one of H, OH, a leaving group, and a probe group; l is an integer from 3 to 6; m is an integer from 1 to 4; and n is an integer from 0 to 3;

(b) contacting a target molecule capable of specifically binding to a probe group R in formula (I) with the probes in the self-assembled monolayer; and (c) measuring an electrical signal from the target molecule-probe comlex.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
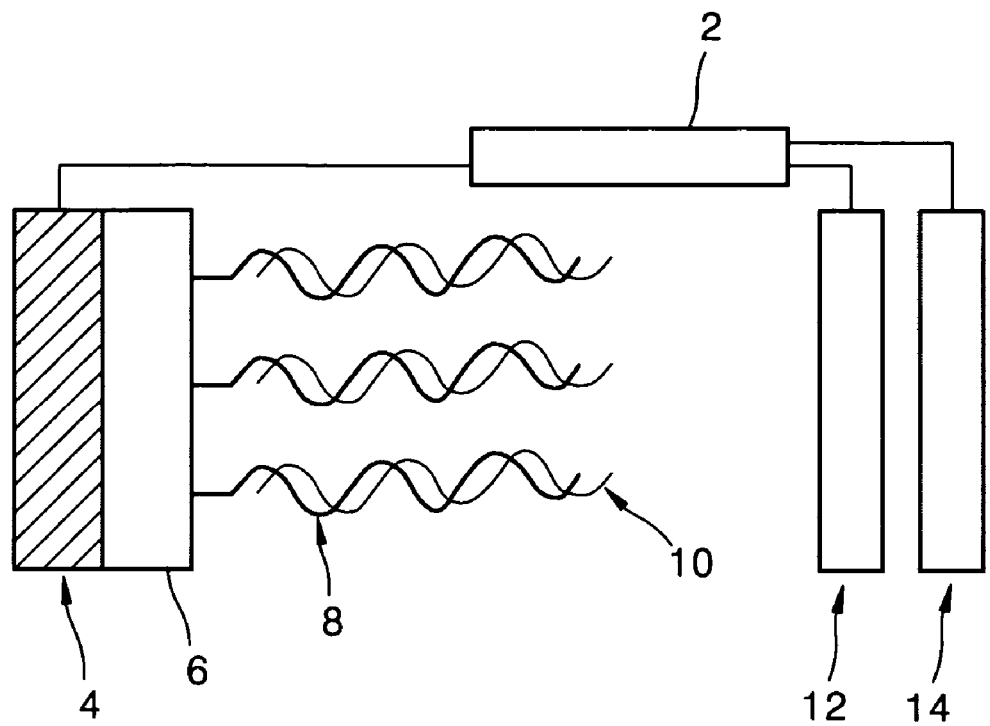
FIG. 1 illustrates an example of a sensor employing an electrode coated with a conductive compound according to the present invention.

The present invention provides a conductive compound of formula (I) below:

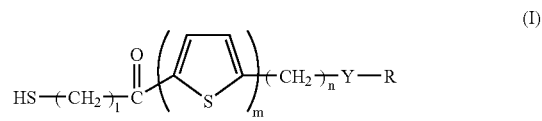

wherein Y is a carbonyl or —NH—; R is one of H, OH, a leaving group, and a probe group; l is an integer from 3 to 6; m is an integer from 1 to 4; and n is an integer from 0 to 3.

The terms "leaving group" used throughout the specification refers to a group that is highly liable to leave due to a nucleophilic substitution reaction. Examples of such leaving groups include a hydroxysuccinimidyl group, a hydroxyphthalimidyl group, a pentafluorophenolyl group, a 4-chlorobenzyl alcoholic group, $TsO^-$, $I^-$, $Br^-$, and $Cl^-$.

The term "probe" used throughout the specification refers to a compound capable of specifically binding to a target compound. Examples of such probes includes a nucleic acid and a protein, and more particularly, a deoxyribonucleic acid (DNA), a ribonucleic acid (RNA), a peptide nucleic acid (PNA), an antibody, an antigen, an enzyme, a cofactor, and a substrate.

The conductive compound of the present invention of formula (1), which is electrically conductive, may be coated on a gold electrode and may be used in a sensor. The electrode or sensor may be used in detecting a particular compound using an electrical signal generated from a target molecule-probe complex. The compound may also be used in a target molecule detecting method using the electrode or the sensor.

Preferred conductive compounds according to the present invention include a compound of formula (II) below, which is correspond to a compound of formula (1) wherein Y is carbonyl group, R is OH, I=5, m=1 and n=1 and a compound of formula (II) below, which is correspond to a compound of formula (1) wherein Y is carbonyl group, R is a hydroxyphthalimidyl group, I=5, m=3 and n=1.

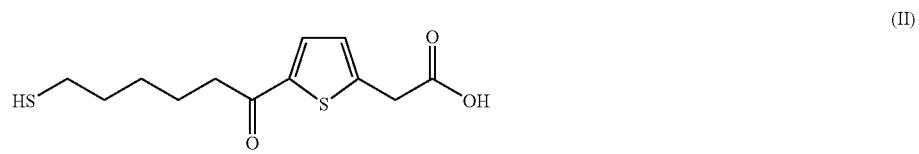

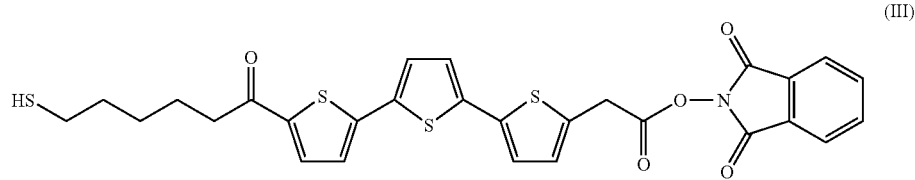
The compound of formula (II) may be synthesized as follows.
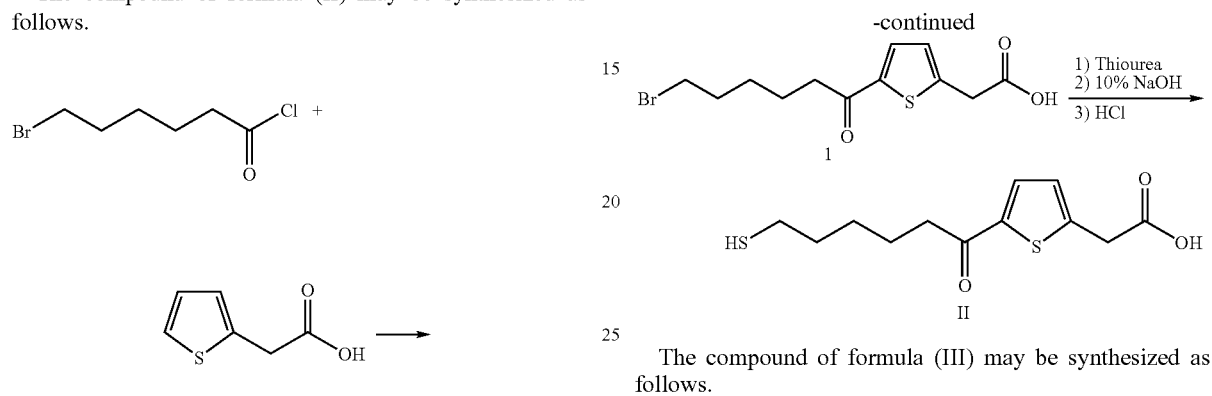
The compound of formula (III) may be synthesized as follows.
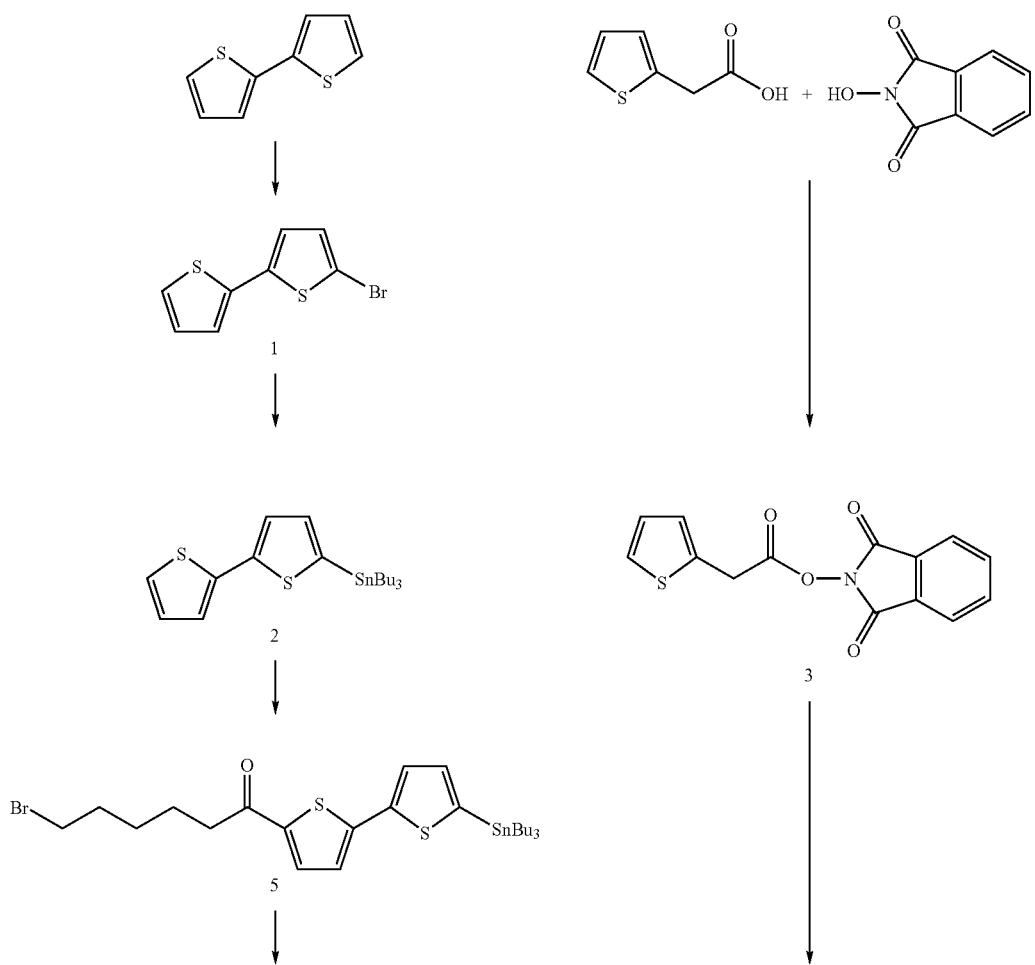

-continued

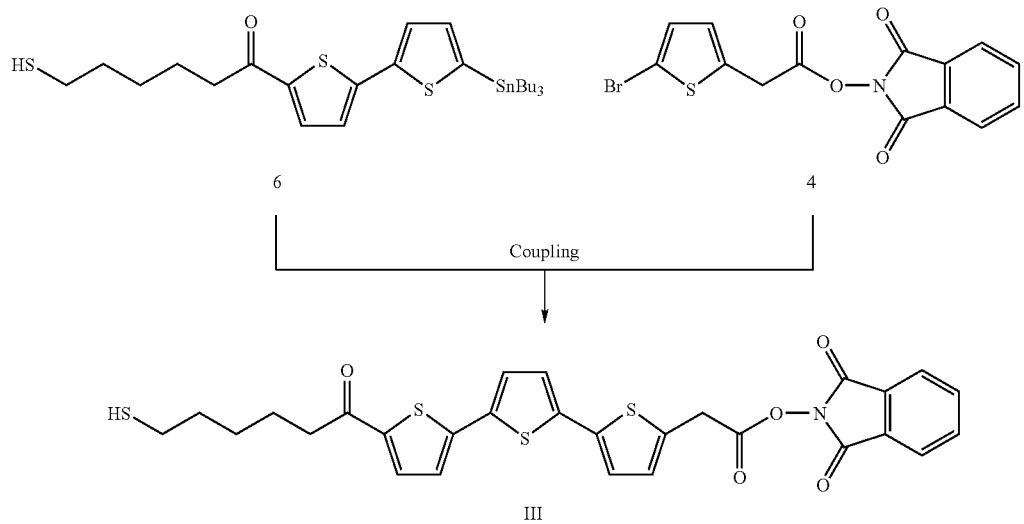

Coupling

III

The present invention provides a method of synthesizing the compound of formula (I) above by reacting a compound of formula (IV) below with thiourea.

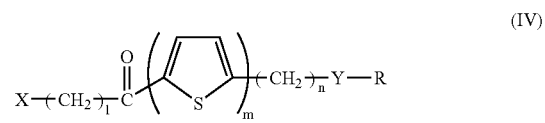
(IV)

wherein Y is a carbonyl or —NH— group, R is one of H, OH, a leaving group, and a probe group, X is halogen atom, l is an integer from 3 to 6, m is an integer from 1 to 4, and n is an integer from 0 to 3.

Preferred examples of the leaving group in formula (IV) include a hydroxysuccinimidyl group, a hydroxyphthalimidyl group, a pentafluorophenolyl group, and a 4-chlorobenzyl alcoholic group. The compound of formula (IV) may be reacted with thiourea in a basic condition, followed by neutralization.

The present invention also provides a method of synthesizing the compound of formula (I) above by reacting a compound of formula (V) below and a compound of formula (VI) below.

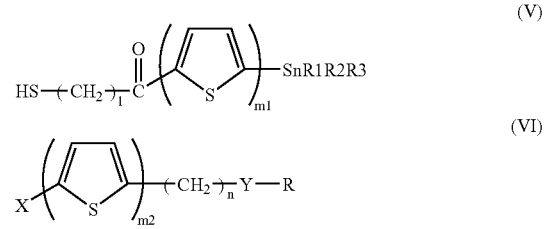

R1, R2, and R3 are independently $C_1$–$C_8$ alkyl groups; Y is a carbonyl or —NH— group; R is one of H, OH, a leaving group, and a probe group; X is a halogen atom; l is an integer from 3 to 6; m1 and m2 are integers from 1 to 4 and $2 \leq m1+m2 \leq 4$; and n is an integer from 0 to 3. Preferred examples of the leaving group include a hydroxysuccinimidyl group, a hydroxyphthalimidyl group, a pentafluorophenolyl group, and a 4-chlorobenzyl alcoholic group.

The present invention also provide an electrode coated with the conductive compound. Materials commonly used for electrodes, such as gold, may be used to manufacture the electrode according to the present invention.

The present invention provides a sensor including the electrode coated with the conductive compound. The sensor according to the present invention comprises common sensor components, for example, a working electrode, a counter electrode, and a reference electrode, in addition to the electrode coated with the conductive compound.

FIG. 1 illustrates an example of a sensor including an electrode coated with the conductive compound according to the present invention. As illustrated in FIG. 1, the sensor includes a working electrode 4, which is coated with a conductive compound 6 according to the present invention and to which probes 8 are covalently bonded, a counter electrode 12, a reference electrode 14, and an electrostatic voltmeter 2. The working electrode 4, which is coated with the conductive compound according to the present invention and to which the probes 8 are covalently bonded, may be formed as follows.

A method of manufacturing an electrode according to the present invention, which is coated with the conductive compound and probes, such as DNA, are immobilized on, includes immobilizing the conductive compound of formula (I) with R selected from among H, —OH, a hydroxysuccinimidyl group, a hydroxyphthalimidyl group, a pentafluorophenolyl group, and a 4-chlorobenzyl alcoholic group to form a self-assembled monolayer on a substrate, and covalently binding the probes 8, which may be DNA, to the self-assembled monolayer. Alternatively, the electrode according to the present invention may be manufactured by just immobilizing on a substrate a conductive compound of formula (I) above with R that is a probe group to form a self-assembled monolayer.

A target molecule 10 in a sample can be detected using the sensor according to the present invention. When the probes 8 immobilized on the working electrode 4 of the sensor are made to contact the sample and hybridized with the target molecule 10, a voltage or current level read by the sensor varies depending on the hybridized result so that the target molecule 10 can be detected from the variation.

Voltage or current variations occurring from hybridization are thought to follow, though not absolutely, the mechanism described below. The electrical current at a particular redox potential depends on the delocalization in the electrically conductive polymer on the substrate. The degree of delocalization in the electrically conductive polymer after a target molecule hybridizes to the probe that is covalently bonded to the electrically conductive polymer according to the present invention is smaller than before the hybridization. Accordingly, when a target molecule hybridizes to a probe, the electrical current decreases. Therefore, a target molecule in a sample can be detected by measuring a decrease in the amount of redox potential that occurs when the target molecule hybridizes to a probe or an increase when not.

Figure 2:
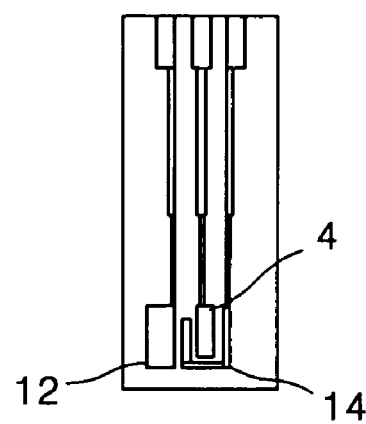
FIG. 2 illustrates another example of a sensor employing an electrode coated with the conductive compound according to the present invention.

FIG. 2 illustrates another example of a sensor including an electrode coated with the conductive compound according to the present invention. The sensor includes a working electrode 4, a counter electrode 12, and a reference electrode 14. The working electrode 4 is coated with the conductive compound according to the present invention.

The present invention provides a method of detecting a target molecule using the conductive compound of the present invention. The method includes: (a) immobilizing a compound of formula (I) below on a gold substrate to form a self-assembled monolayer;

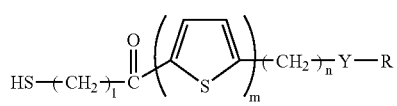

wherein Y is a carbonyl or —NH—; R is one of H, OH, a leaving group, and a probe group; l is an integer from 3 to 6; m is an integer from 1 to 4; and n is an integer from 0 to 3;

(b) reacting a surface of the self-assembled monolayer with probes;

(c) contacting a target molecule capable of specifically binding to the probes with the probes in the self-assembled monolayer; and (d) measuring an electrical signal from the target molecule-probe.

Suitable examples of the leaving group include a hydroxysuccinimidyl group, a hydroxyphthalimidyl group, a pentafluorophenolyl group, and a 4-chlorobenzyl alcoholic group.

Regarding (d) in the above-described method, the target molecule-probe complex may generated by a specific interaction between the target molecule and the probe molecule immobilized on the electrode. The specific interaction includes noncovalent interactions such as hydrophobic bond, hydrogen bond, Van der Wals interactions, and ionic interaction, but not limited to these examples, as well as covalent bond. For example, with the assumption that the target molecule is a DNA having a particular nucleotide sequence, the specific interaction between probe DNA and target DNA are caused to occur via way of hybridization reaction between the two ssDNA molecules. The two ssDNA molecules in the above case generally have a perfect or partially matched complementary nucleotide sequences. When the two DNA molecules have partially matched nucleotide sequences, the conditions for hybridizations, for example, salt concentration and temperature, may be adjusted depending on the sequences.

Another method of detecting a target molecule using the conductive compound of the present invention according to the present invention includes: (a) immobilizing a compound of formula (I) below on a gold substrate to form a self-assembled monolayer;

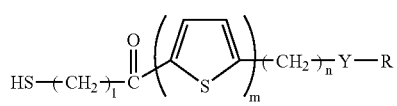

wherein Y is a carbonyl or —NH—; R is one of H, OH, a leaving group, and a probe group; l is an integer from 3 to 6; m is an integer from 1 to 4; and n is an integer from 0 to 3;

(b) contacting a target molecule capable of specifically binding to the probe group R in formula (I) with the probes in the self-assembled monolayer; and (c) measuring an electrical signal from the target molecule-probe complex.

Regarding (c) in the above-described method, the target molecule-probe complex may generated by a specific interaction between the target molecule and the probe molecule immobilized on the electrode. The specific interaction includes noncovalent interactions such as hydrophobic bond, hydrogen bond, Van der Wals interactions, and ionic interaction, but not limited to these examples, as well as covalent bond. For example, with the assumption that the target molecule is a DNA having a particular nucleotide sequence, the specific interaction between probe DNA and target DNA are caused to occur via way of hybridization reaction between the two ssDNA molecules. The two ssDNA molecules in the above case generally have a perfect or partially matched complementary nucleotide sequences. When the two DNA molecules have partially matched nucleotide sequences, the conditions for hybridizations, for example, salt concentration and temperature, may be adjusted depending on the sequences.

Regarding the above-described two methods of detecting a target molecule using a conductive compound according to the present invention, the electrical signal refers to, but is not limited to, a signal measured from voltage or current variations. The probes or the probe group may be nucleic acids or proteins. Specified examples of the probes or the probe group R include a DNA, a RNA, a PNA, an antibody, an antigen, an enzyme, a cofactor, and a substrate.

The present invention will be described in greater detail with reference to the following examples. The following examples are for illustrative purposes and are not intended to limit the scope of the invention.

EXAMPLE 1

Synthesis of Compound of Formula (II)

A compound of formula (II) was synthesized as follows.

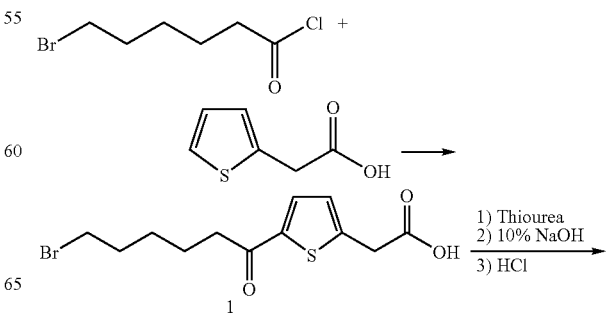

-continued

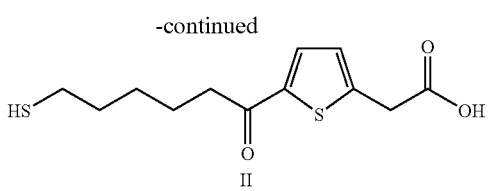

1. Synthesis of Intermediate (1)

312 mg (2.34 mmole) of $AlCl_3$ was added to a mixed solvent of 6 mL of dichlomethane and 6 mL of $CS_2$ in a 30-mL, 2-neck round-bottomed flask and stirred in an argon gas atmosphere. 277 mg (1.95 mmole) of 2-thiopheneacetic acid was dropwise added to A solution of 2 mL of dichloromethane and 2 mL of $CS_2$ over 5 minutes in a water bath to prevent excess heat generation. This mixture was stirred at room temperature for 20 minutes and refluxed for 3 hours.

The resulting product was purified through column chromatography using a 4:1 mixed solvent of chloroform and methanol to provide 410 mg of a white solid intermediate (1) with a yield of 52.7%. The resulting purified intermediate was identified by NMR and FT-IR. The results are as follows.

1H-NMR($CDCl_3$, 400 MHz): δ 7.51 (d, J=4.0 Hz, 1H), 6.92(d, J=4.0 Hz, 1H), 3.82(s, 2H), 3.33(t, J=6.8 Hz, 2H), 2.81(t, J=7.3 Hz, 2H), 1.80(m, 2H), 1.66(m, 2H), 1.43(m, 2H)

FT-IR (KBr): 3430($CO_2H$), 2950, 2845(C—H), 1650 (C=O), 1590, 1450 $cm^{-1}$

2. Synthesis of Compound (II)

204 mg (0.511 mmole) of the intermediate (1) and 78 mg (1.02 mmole) of thiourea were added to 2.0 mL of DMSO contained in a 30-mL, 2-neck round-bottomed flask and stirred in an argon gas atmosphere at room temperature for 12 hours. 3.2 mL of 10% NaOH was added to the mixture and stirred further for 1 hour, followed by pH adjustment to pH=2 or 3 using about 8 mL of 1 M HCl and extraction using ethyl acetate (EtOAc). The extracted product was purified through column chromatography to provide 105 mg of compound (II) with a yield of 75.4%. This compound (II) was identified to be 5-(6-mercapto-hexanoyl)-thiophen-2-yl]-acetic acid (MTPAA) by NMR and FT-IR. The results are as follows.

1H-NMR($CDCl_3$, 400 MHz): δ7.35(d, J=3.3 Hz, 1H), 6.92(s, 1H), 3.60(s, 2H), 2.70(t, J=7.1 Hz, 2H), 2.42(m, 2H), 1.25–1.65(m, 6H)

FT-IR(KBr): 3430($CO_2H$), 2950, 2840(C—H), 1650 (C=O), 1580, 1450 $cm^{-1}$

EXAMPLE 2

Synthesis of Compound (III)

A compound of formula (II) was synthesized as follows.

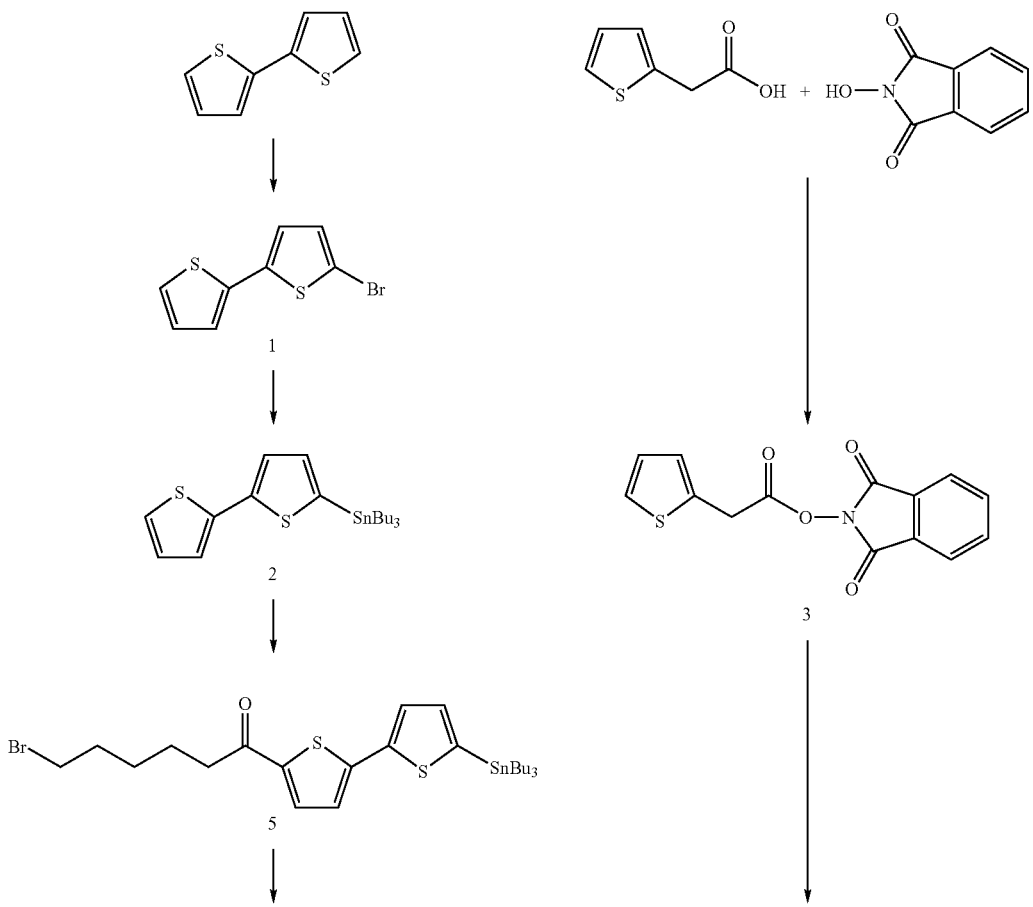

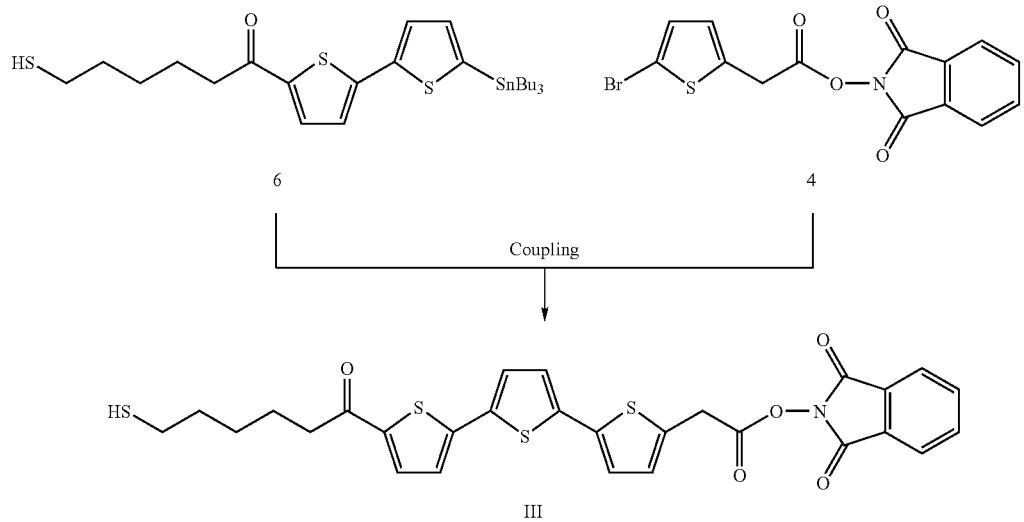

1. Synthesis of Intermediate (1)

3 g (18 mmol) of 2'2-bithiophene and 50 mL of DMF were placed in a 250-mL, 2-neck round-bottomed flask and stirred. A solution of 3.2 g (18 mmol) of N-bromsuccimide (NBS) in 10 mL of DMF was dropwise added to the mixture in an ice bath.

After completion of the reaction, the reaction product was extracted using methylene chloride and recrystallized using methanol (MeOH) to obtain 2.5 g of a light yellow solid compound with a yield of 56%. This intermediate (1) was identified by NMR. The results are as follows.

$^1$HNMR (CDCl$_3$ 400 MHz): δ=6.91(1H, d), 6.96(1H, d), 7.00(1H, dd), 7.22(1H)

2. Synthesis of Intermediate (2)

3 g (12 mmol) of the intermediate (1) and tetrakis triphenyl phosphine palladium (Pd(PPh$_3$)$_4$) were dissolved in 50 mL of purified toluene while stirring it. 4.76 g (12 mmol) of tributyltin chloride was dropwise added to the mixture and reacted at 80° C. for 4 hours. After completion of the reaction, the reaction product was purified through column chromatography using hexane to provide 4.2 g of a light green solid compound with a yield of 78%. This intermediate compound (2) was identified by NMR and FR-IR. The results are as follows.

$^1$HNMR (CDCl$_3$ 400 MHz): δ=7.19(1H, d), 7.10(1H, d), 6.98(1H, d), 6.85(1H, d), 6.82(1H, d), 1.60(6H, m), 1.30 (12H, m), 0.90(9H, t)

FT-IR (KBr): 2950, 2850(C—H), 1590(C=C), 1450(C—H), 1375(C—H) cm$^{-1}$

3. Synthesis of Intermediate (3)

3 g (21.1 mmol) of 2-thiophene acetic acid and 3.44 g (21.1 mmol) of N-hydroxyphalimide were added to 50 mL of chloroform and stirred. 4.35 g (21.1 mmol) of 1,3-Dicyclohexylcarbodiimide (DCC) was added to the mixture and stirred for 3 hours. After completion of the reaction, trituration was performed with hexane to obtain 5.8 g of a white solid compound with a yield of 91%. This intermediate (2) was identified by NMR and FT-IR. The results are as follows.

$^1$HNMR (CDCl$^3$ 400 MHz): δ=7.80(4H, dd), 7.25(1H, d), 7.10(1H, d), 7.00(1H, d), 4.20(2H, s)

FT-IR(KBr): v=1741, 1359, 1139 cm$^{-1}$

4. Synthesis of Intermediate (4)

5.4 g (17.9 mmol) of the intermediate (3) was placed in 50 mL of DMF and stirred. 3.17 g (17.8 mmol) of NBS was added to the mixture and stirred further for 3 hours. After completion of the reaction, extraction with methylene chloride and column chromatography with methylene chloride were performed to obtain 3.57 g of yellowish white solid with a yield of 52%. This intermediate (4) was identified by NMR and FT-IR. The results are as follows.

$^1$HNMR(CDCl$_3$ 400 MHz): δ=7.80(4H, dd), 6.90(1H, d), 6.80(1H, d) 4.10(2H,s)

FT-IR(KBr): v=1743, 1363, 1074 cm$^{-1}$

5. Synthesis of Intermediate (5)

0.7 g (5.3 mmol) of AlCl$_3$ was dissolved in 10 mL of CS$_2$ and 10 mL of methylene chloride and stirred. 2 g (5.55 mmol) of intermediate (2) was dissolved in a mixture of 3 mL of CS$_2$ and 3 mL of methylene chloride and dropwise added to the stirred solution. 0.67 mL of 6-bromohexaonyl chloride was dropwise added to the mixture and refluxed overnight. After completion of the reaction, column chromatography with methyleno chloride was performed to obtain 1.7 g of a yellow solid compound with a yield of 70%. This intermediate (5) was identified by NMR and FT-IR. The results are as follows.

$^1$HNMR(CDCl$_3$ 400 MHz): δ=8.0(1H, s), 7.5(1H, d), 7.15–6.95(2H, t), 3.40(2H, t), 1.9(2H, t), 1.8–1.25(26H, m), 0.9(9H, t)

FT-IR(KBr): 2950, 2850(C—H), 1650(C=O), 1590 (C=O), 1450(C—H), 1375(C—H) cm$^{-1}$

6. Synthesis of Intermediate (6)

1.7 g (3.16 mmol) of intermediate (5) and 0.48 g (6.32 mmol) of thiourea were dissolved in 30 mL of DMSO and stirred at room temperature for 12 hours. 10 mL of 10% NaOH was added to the mixture and stirred further for 1 hour, followed by pH adjustment to pH 2–3 using 1 M HCl. Extraction with ethyl acetate (EtOAc) and recrystallization with hexane were performed to obtain 0.9 g of a yellow solid compound with a yield of 58%. This intermediate (6) was identified by NMR and FT-IR. The results are as follows.

$^1$HNMR(CDCl$_3$ 400 MHz): δ=7.5(1H, s), 7.3(1H, d), 7.15–6.95(2H, t), 2.85(2H, t), 2,7(2H, t), 2.5(1H,t) 1.8–1.1 (24H, m), 0.9(9H, t)

FT-IR (KBr): 2950, 2850(C—H), 1645(C=O), 1588 (C=O), 1450(C—H), 1375(C—H) cm$^{-1}$

EXAMPLE 3

Formation of Self-Assembled Monolayer Using the Compound (MTPAA) of Formula (I) and Immobilization of Probes 1. Formation of Self-Assembled Monolayer A self-assembled monolayer (SAM) was formed by immobilizing the compound (MTPAA) of formula (I) on a gold (Au) plate. Initially, the Au electrode plate was polished using an alumina slurry having particle diameters of 0.05 μm, 0.3 μm, and 0.5 μm, respectively and subjected to 80 times of electrochemical surface activation treatments (−0.1~+1.5 V, 200 mv/s) in a 1.0M $H_2SO_4$ solution. Next, the Au electrode plate was immersed in a solution of 1 mM thiophene dissolved in dimethylsulfoxide (DMSO) for 15 hours to form the SAM. Due to a greater refractive index (nD20=1.479) of DMSO, a resonance angle could not be measured to confirm the formation of the SAM. Instead, the formation of the SAM of the MTPAA on the Au plate was confirmed using an electrochemical method and FTIR-RAS.

Figure 3:
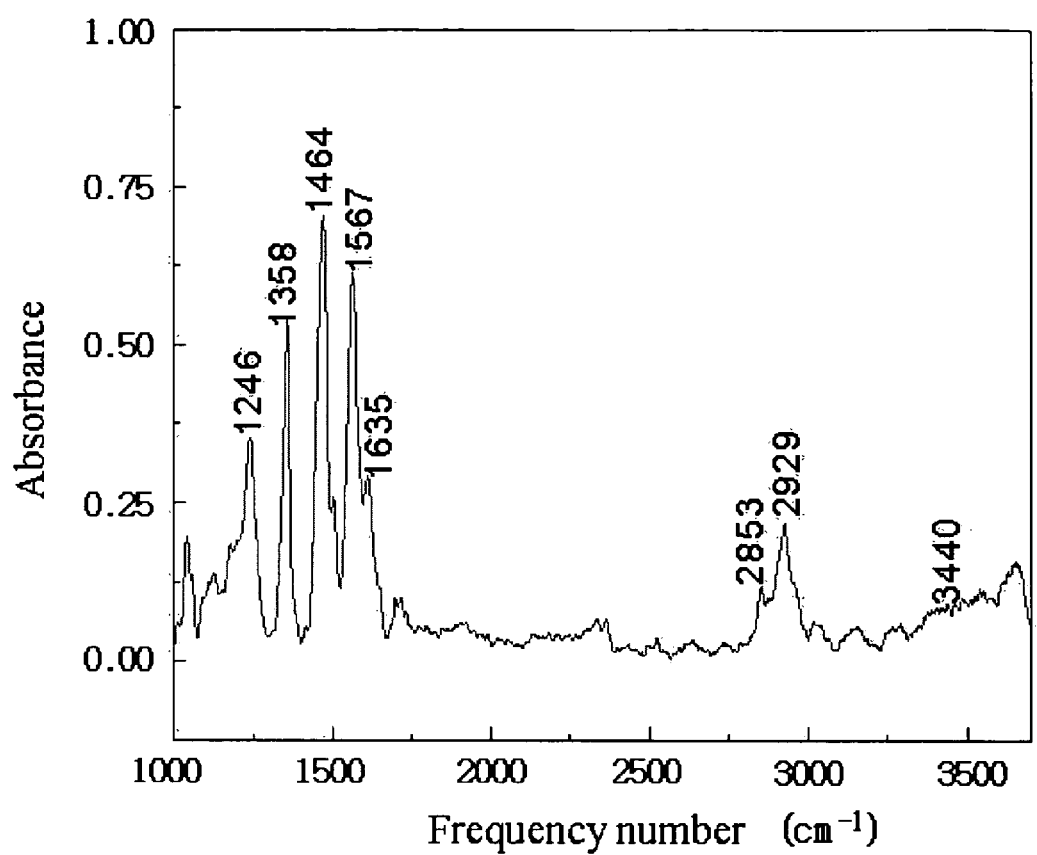
FIG. 3 is a graph illustrating the result of FTIR analysis on an MTPAA monolayer on a gold thin layer.

According to the FTIR-RAS spectrum analyzed at an angle of incidence of 80 degrees, peaks from the SAM were shifted toward a lower frequency domain than a KBr pellet. The C—H stretching mode was observed near 2850–2060 cm$^{-1}$ in the spectrum, confirming the formation of the SAM of MTPAA in a regular pattern on a surface of the Au plate. The formation of the SAM as a regular pattern was confirmed using a relative band intensity between symmetry and asymmetry C—H stretching modes. The results are shown in FIG. 3.

2. Immobilization of Probes ssDNA (5'-NH$_2$-GTTCTTCTCATCATC-3': SEQ. NO: 1) with an amino group at the 5'-terminal was immobilized as probes on the SAM of MTPAA and analyzed using surface plasmon resonance (SPR). The probe DNA was immobilized using N-hydroxysuccinimide (NHS) and 1-(3-Dimethylaminopropyl)-3-ethylcarbodiimide hydrochloride (EDC) to substitute the carboxyl group of the MTPAA with NHS, known as a good leaving group, and form amide bonds. This single process of immobilization using NHS, EDC, and ssDNA is known (Langmuir 16, 3272, 2000).

Figure 4:
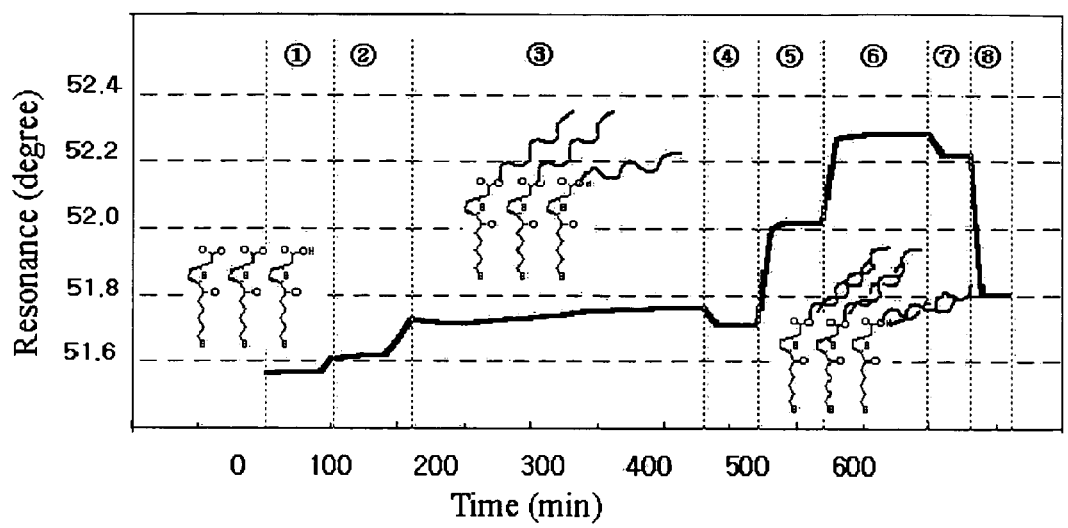
FIG. 4 is a sensogram of resonance angle versus time, which was measured through formation of a monolayer, immobilization of probes, and hybridization of DNA.

FIG. 4 is a graph of resonance angle versus time obtained through the formation of the SAM, immobilization of the probes, and hybridization with a target DNA. In FIG. 4, ① indicates the resonance angle of the Au plate in a plain PBS buffer after the formation of the SAM of MTPAA, ② indicates the resonance angle of the Au plate with the SAM in a PBS buffer containing NHS and EDC, ③ indicates the resonance angle of the Au plate in a PBS buffer containing the probe ssDNA for immobilization, ④ indicates the resonance angle of the Au plate washed with a PBS buffer after the immobilization of the probe ssDNA, ⑤ indicates the resonance angle of the Au plate when a plain TE buffer was injected, ⑥ indicates the resonance angle of the Au plate when a TE buffer containing a target ssDNA was injected, ⑦ indicates the resonance angle of the Au plate when a TE buffer was injected for washing after the hybridization, and ⑧ indicates the resonance angle of the Au plate when the TE buffer was replaced with a PBS buffer.

As shown in FIG. 4, the resonance angle was 51.560 when the plain PBS buffer was injected to stabilize the Au plate having the SAM of MTPAA and 51.620 when the PBS buffer containing NHS and EDC was injected. The resonance angle increased to 51.732 when the PBS buffer containing the probe ssDNA was injected. The resonance angle decreased slowly after reaction with the probe ssDNA, increased gradually with time, and was saturated at 51.762 degrees. This tendency of resonance angle variations is attributed to that the probe ssDNA physically adsorbed into the SAM of MTPAA being more stabilized due to chemical adsorption.

The resonance angle was shifted by 0.141 degrees after the immobilization of the probe ssDNA, from 51.560 degrees after the formation of the SAM of MTPAA to 51.701 degrees after the immobilization of the probe ssDNA and washing with the PBS buffer. This shift of the resonance angle results from variations in the refractive index and the thickness of the SAM of MTPAA, indicating that the probe ssDNA was immobilized on the SAM of MTPAA.

The resonance angle increased to 52.017 when the TE buffer was injected and to 52.269, when the target ssDNA was injected. The resonance angle increased gradually and saturated at 52.285, due to hybridization. The resonance angle dropped to 52.221 after washing with the TE buffer, which was performed to remove non-specific bonds. To compare the resonance angle after the hybridization of the target ssDNA to the probe DNA with the resonance angle after the immobilization of the probe DNA, the TE buffer was replaced with the PBS buffer. The resonance angle of the Au plate in the PBS buffer after the hybridization of the target ssDNA to the probe DNA was 51.802, indicating that the resonance angle was shifted to the right by 0.252 degrees due to the TE buffer. It is confirmed from the shift of the resonance angle from 51.701 after the immobilization of the probe DNA in the PBS buffer to 51.802 in the PBS buffer after the hybridization that complementary bonds were formed between the probe DNA and the target ssDNA.

EXAMPLE 4

Formation of SAM of the Compound (MTPAA) Having Formula (I), Immobilization of Probes, Hybridization of Target DNA, and Electrochemical Characteristics Measurement 1. Formation of Compound of Formula (I)

A self-assembled monolayer (SAM) was formed by immobilizing the compound (MTPAA) of formula (I) on an Au electrode. Initially, the Au electrode plate was polished using an alumina slurry having particle diameters of 0.05 μm, 0.3 μm, and 0.5 μm, respectively and subjected to 80 times of electrochemical surface activation treatments (−0.1~+1.5 V, 200 mv/s) in a 1.0M $H_2SO_4$ solution. Next, the Au electrode plate was immersed in a solution of 1 mM thiophene dissolved in DMSO for 15 hours to form the SAM.

2. Immobilization of ssDNA ssDNA was immobilized on the SAM as follows.

1) The SAM on the Au electrode was reacted with a 50 mM phosphate buffer solution (pH 7.40) containing 2 mM EDC and 5 mM NHS to form linkers.

2) The Au electrode was washed with 50 mM phosphate buffer (pH 7.40).

3) 20 μl of a 0.5M acetate buffer solution (pH 4.8) containing 100 ppm of probe ss DNA was dropped onto a surface of the SAM with the linkers.

4) The resulting structure was dried overnight in air, immersed in distilled water for 2 hours, and washed with distilled water.

3. Hybridization of target DNA 1) 20 μl of a 20 mM Tris buffer solution (pH 7.00) containing 100 ppm of a target DNA was dropped onto a surface of the Au electrode on which the probe ssDNA had been immobilized.

2) The resulting Au electrode was dried in air for 30 minutes.

4. Cyclic Voltammetry

The Au electrode was washed with a phosphate buffer and methanol after reaction in each step, dried using a $N_2$ gas, without using dopants conventionally used together with conductive polymers, and washed with dichloromethane ($CH_2Cl_2$).

Cyclic voltammetry was performed in an electrolyte solution of 0.1 M $Et_4$ $NBF_4$/$CH_2Cl_2$ using an Ag/AgCl electrode as a reference electrode and a Pt-wire electrode as a counter electrode in a potential range of 100–1200 mV at a scan rate of 200 mV/s. After each measurement and before a next process, the Au electrode was washed with $CH_2Cl_2$ three times, dried, and washed again with the phosphate buffer. Use of the organic solvent $CH_2Cl_2$ and the electrolyte $Et_4NBF_4$/$CH_2Cl_2$ avoids unwanted reactions in a voltage range of measurement of –0.1–1.2V, such as oxidation and reduction occurring when using water at a voltage of 1V or greater.

Figure 5:
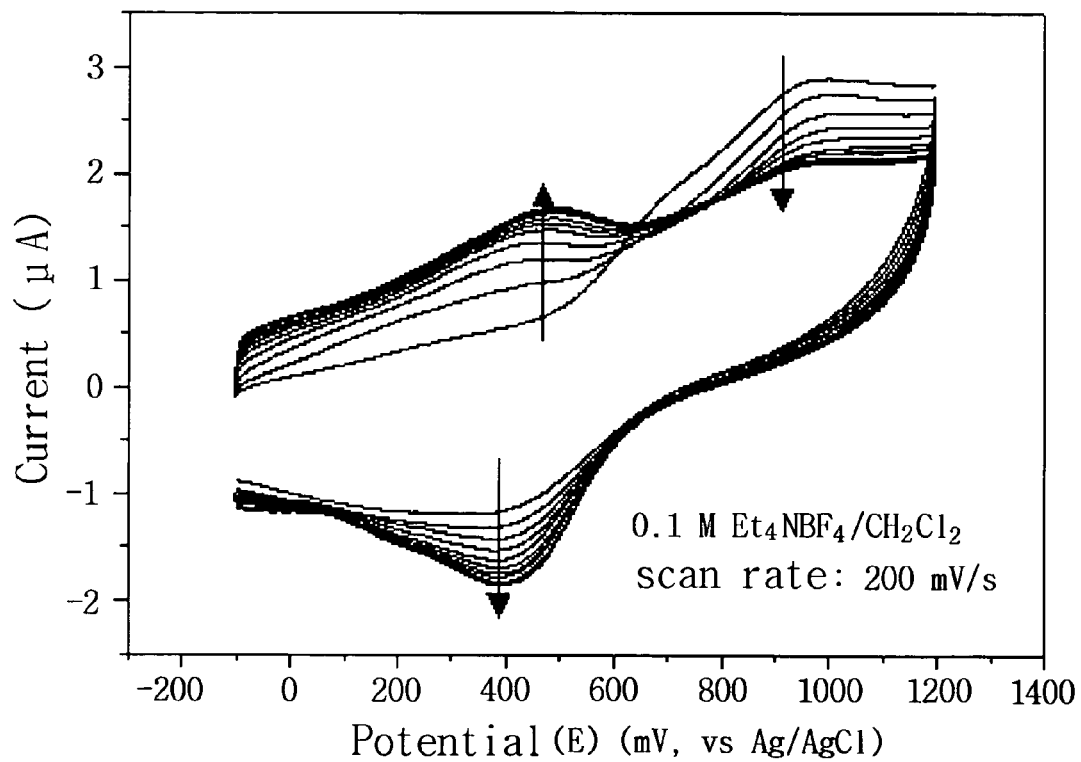
FIG. 5 is a cyclic voltammogram of an MTPAA monolayer.

FIG. 5 is a cyclic voltammogram of the SAM of MTPAA obtained through 13 measurements. In a cyclic voltammogram measured first, an anodic peak appeared at 980 mV and a cathodic peak appeared at 420 mV. The anodic peak at 980 mV decreased while the cathodic peak at 420 mV increased with increasing number of measurements. A new cathodic peak appeared at 480 mV. Stabilized, constant cyclic voltammograms were obtained after 13 measurements.

Figure 6:
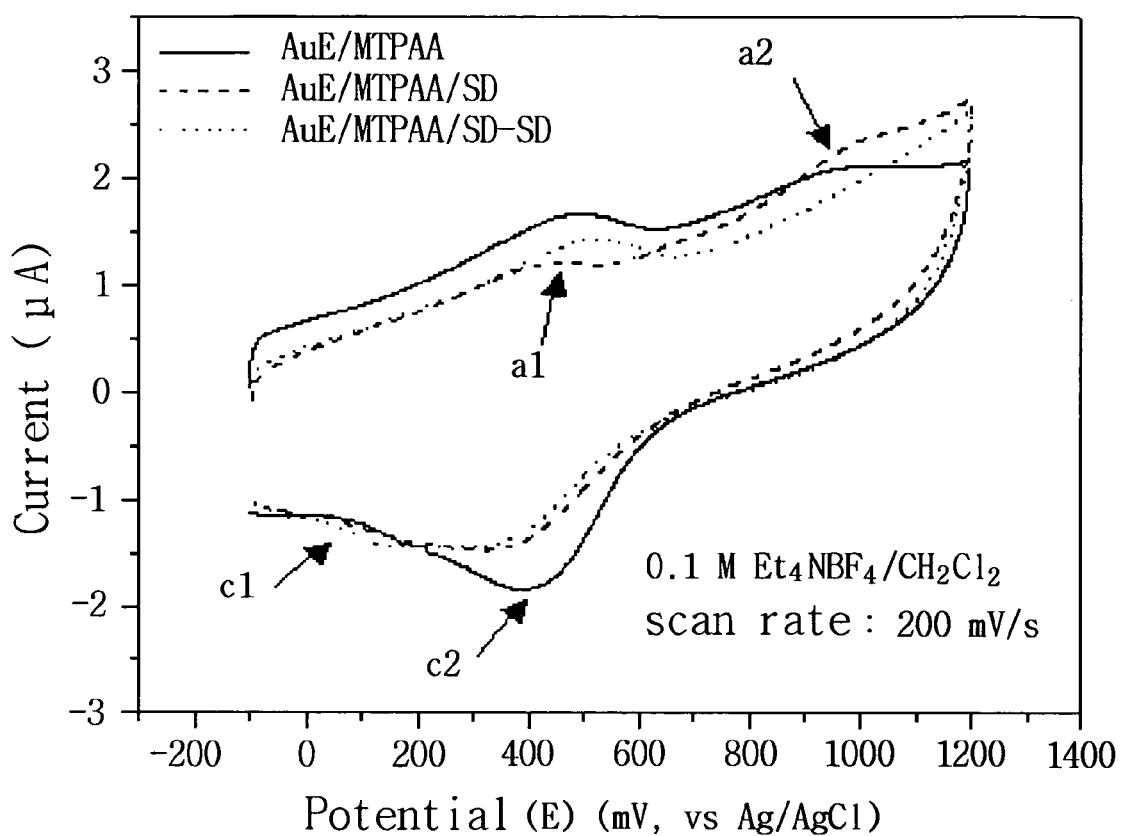
FIG. 6 is a cyclic voltammogram measured after the immobilization of ssDNA probes, following the treatment of an electrochemically stabilized MTPAA monolayer with HNS/EDC.

FIG. 6 is a cyclic voltammogram measured using the same method described above after the immobilization of the probe ssDNA on the SAM of MTPAA electrochemically stabilized and treated with NHS and EDC. Comparing with the cyclic voltammogram of the SAM of MTPAA before hybridization shown in FIG. 5, an anodic peak a1 had a smaller current value of 180 nA and a smaller voltage value of 89 mV, an anodic peak a2 had a larger current value of 110 nA and a larger voltage value of 24 mV, and a cathodic peak c1 had a smaller current value of 680 nA and a smaller voltage value of 51 mV.

Comparing a cyclic voltammogram measured after the hybridization of a target DNA to the probe ssDNA, in FIG. 6, with the above-described cyclic voltammogram measured after the immobilization of the probe ssDNA, the current value of the anodic peak a1 increased to 190 nA, and the voltage value thereof increased to 89 mV. The anodic peak c2 which had appeared when probe ssDNA had been immobilized disappeared after the hybridization of the target DNA to the probe ssDNA, and a new cathodic peak c2 having a current value of 100 nA appeared at 155 mV. No variation appeared in the cathodic peak c1.

The above-described results of the cyclic voltammography are tabled in Table 5 below. The reproducibility of the cyclic voltammography was confirmed by performing 4 measurements on each of three sets of electrodes.

TABLE 5

Voltage values and current values of anodic peaks and cathodic peaks measured in each step

| | Anodic Peak | | | | Cathodic Peak | | | |
|---|---|---|---|---|---|---|---|---|
| | a1 | | a2 | | c1 | | c2 | |
| | Ep | Ip | Ep | ip | Ep | ip | Ep | ip |
| AuE/ MTPAA | 483 | 270 | 957 | 220 | 409 | –1280 | X | X |
| AuE/ MTPAA/ SD | 394 | 90 | 981 | 330 | 358 | –680 | X | X |
| AuE/ MTPAA/ SD-SD | 483 | 280 | X | X | 360 | –670 | 155 | 100 |

As shown in Table 5 above, when a probe ssDNA is immobilized on the monolayer of the present compound, the anodic and cathodic peaks change as follows: decreased current and voltage values of the anodic peak a1, increased current and voltage values of the anodic peak a2, and reduced current and voltage values of the cathodic peak c1, with respect to those values before immobilization, and these changes are indicative of the immobilization of the probe ssDNA. In addition, when a target ssDNA is hybridized with the probe ssDNA, the anodic and cathodic peaks change as follows: increased current and voltage values of the anodic peak a1, disappearance of the anodic peak a2 which had been appeared due to immobilization of a probe ssDNA, no variation in current and voltage values of the cathodic peak c1, and an appearance of a new cathodic peak c2, and these changes are indicative of the hybridization of a target DNA to the probe DNA.

Thus, the conductive compound of the present invention can be used in the manufacture of an electrode and a sensor having a resposivity and stability.

The electrode and sensor of the present invention can be used in the detection of a target molecule with high sensitivity and reproducibility.

The method of detecting a target molecule can efficiently detect a target molecule in a sample.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A conductive compound of formula (I) below:

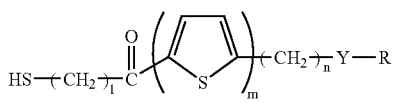

wherein Y is a carbonyl or —NH—; R is one of H, OH, a leaving group, and a probe group; l is an integer from 3 to 6; m is an integer from 1 to 4; and n is an integer from 0 to 3.

2. The conductive compound of claim 1, wherein the probe group is a nucleic acid or a protein.

3. The conductive compound of claim 2, wherein the probe group is selected from the group consisting of a deoxyribonucleic acid (DNA), a ribonucleic acid (RNA), a peptide nucleic acid (PNA), an antibody, an antigen, an enzyme, a cofactor, and a substrate.

4. A method of synthesizing the conductive compound of said formula (I) of claim 1 by reacting a compound of formula (IV) below with thiourea:

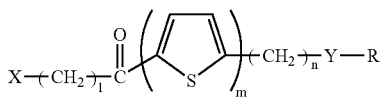

wherein Y is carbonyl or —NH—, R is one of H, OH, a leaving group, and a probe group, X is halogen atom, l is an integer from 3 to 6, m is an integer from 1 to 4, and n is an integer from 0 to 3.

5. A method of synthesizing the conductive compound of formula (I) of claim 1, comprising reacting a compound of formula (V) below with a compound of formula (VI) below:

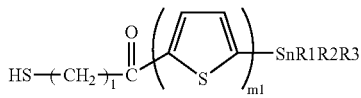

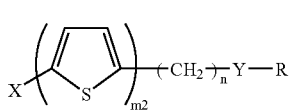

wherein R1, R2, and R3 are independently $C_1$–$C_8$ alkyl groups; Y is carbonyl or —NH— group; R is one of H, OH, a leaving group, and a probe group; X is a halogen atom; l is an integer from 3 to 6; m1 and m2 are integers from 1 to 4 and $2 \leq m1+m2 \leq 4$; and n is an integer from 0 to 3.

6. An electrode coated with the conductive compound of said formula (I) of claim 1, the electrode being made of gold.

7. A sensor including an electrode coated with the conductive compound of said formula (I) of claim 1, the electrode being made of gold.

8. A target molecule detection method comprising:

(a) immobilizing a compound of formula (I) below on a gold substrate to form a self-assembled monolayer;

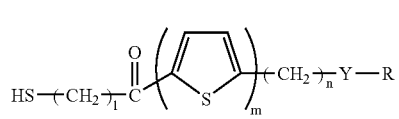

wherein Y is a carbonyl or —NH—; R is one of H, OH, a leaving group, and a probe group; l is an integer from 3 to 6; m is an integer from 1 to 4; and n is an integer from 0 to 3;

(b) reacting a surface of the self-assembled monolayer with probes;

(c) contacting a target molecule capable of specifically binding to the probes with the probes in the self-assembled monolayer; and (d) measuring an electrical signal from the target molecule-probe complex.

9. A target molecule detection method comprising:

(a) immobilizing a compound of formula (I) below on a gold substrate to form a self-assembled monolayer;

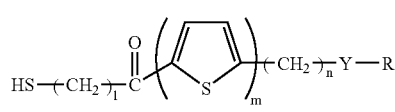

wherein Y is a carbonyl or —NH—; R is one of H, OH, a leaving group, and a probe group; l is an integer from 3 to 6; m is an integer from 1 to 4; and n is an integer from 0 to 3;

(b) contacting a target molecule capable of specifically binding to a probe group R in formula (I) with the probes in the self-assembled monolayer; and (c) measuring an electrical signal from the target molecule-probe comlex.

10. The method of claim, wherein the electrical signal is measured from voltage or current variations.

11. The method of claim, wherein the probes or the probe group is selected from the group consisting of a deoxyribonucleic acid (DNA), a ribonucleic acid (RNA), a peptide nucleic acid (PNA), an antibody, an antigen, an enzyme, a cofactor, and a substrate.

12. The method of claim 8, wherein the target molecule is a nucleic acid or a protein.

13. The method of claim 9, wherein the electrical signal is measured from voltage or current variations.

14. The method of claim 9, wherein the probes or the probe group is selected from the group consisting of a deoxyribonucleic acid (DNA), a ribonucleic acid (RNA), a peptide nucleic acid (PNA), an antibody, an antigen, an enzyme, a cofactor, and a substrate.

15. The method of claim 9, wherein the target molecule is a nucleic acid or a protein.

* * * * *